US007067143B2

(12) United States Patent
Doty et al.

(10) Patent No.: US 7,067,143 B2
(45) Date of Patent: Jun. 27, 2006

(54) PREMIXED AMIODARONE PARENTERAL SOLUTION AND METHOD FOR MAKING THE SAME

(75) Inventors: Mark J. Doty, Grayslake, IL (US); Christine L. Rebbeck, Algonquin, IL (US); James E. Kipp, Wauconda, IL (US); Neervalur V. Raghavan, Northbrook, IL (US)

(73) Assignee: Baxter International, Inc., Deerfield, IL (US)

( * ) Notice: Subject to any disclaimer, the term of this patent is extended or adjusted under 35 U.S.C. 154(b) by 0 days.

(21) Appl. No.: 09/945,374

(22) Filed: Aug. 31, 2001

(65) Prior Publication Data

US 2002/0143050 A1 Oct. 3, 2002

Related U.S. Application Data

(63) Continuation-in-part of application No. 09/822,767, filed on Mar. 29, 2001.

(51) Int. Cl.
*A61K 9/00* (2006.01)
*A61K 9/08* (2006.01)

(52) U.S. Cl. .................. 424/423; 424/426; 424/422
(58) Field of Classification Search ................ 424/489, 424/422
See application file for complete search history.

(56) References Cited

U.S. PATENT DOCUMENTS 5,234,949 A    8/1993   Ehrenpreis et al.
6,030,998 A    2/2000   Somberg
6,143,778 A *  11/2000  Gautier et al. ............... 514/469

FOREIGN PATENT DOCUMENTS

FR    WO 97/02031     1/1997
WO    WO 01/74395 A3  10/2001
WO    WO 01/74395 A2  10/2001

OTHER PUBLICATIONS

Boury, F., et al., "*Interfacial Properties of Amiodarone: The Stabilizing Effect of Phosphate Anions,*" Colloids and Surfaces B: Biointerfaces 20 (2001), pp. 219–227.

Weir, S. J., et al., "*Sorption of Amiodarone to Polyvinyl Chloride Infusion Bags and Administration Sets,*" American Journal of Hospital Pharmacy, vol. 42, Dec., 1985, pp. 2679–2683.

Campbell, Suzanne, et al., "*Stability of Amiodarone Hydrochloride in Admixtures With Other Injectable Drugs,*" American Journal of Hospital Pharmacy, vol. 43, Apr., 1986, pp. 917–921.

* cited by examiner

*Primary Examiner*—Thurman K. Page
*Assistant Examiner*—Rachel M. Bennett
(74) *Attorney, Agent, or Firm*—Paula J. Kelly; Joseph P. Reagen; Bell, Boyd & Lloyd LLC

(57) ABSTRACT

A premix parenteral solution for intravenous administration having amiodarone, as an active ingredient, solubilized in a solution of water for injection and about 0.4–12 mg/ml of a non-ionic surfactant to a concentration range of from 0.2 to 6 mg/ml is disclosed. The solution optionally may include an osmotic agent. No dilution of the solution is required before administering to a patient and the sterile packaged solution has an initial pH within the range of from about 2.9 to about 3.2, preferably about 3.1. Additionally, a method for producing an amiodarone solution suitable for intravenous administration is further disclosed.

29 Claims, 4 Drawing Sheets

PREMIXED AMIODARONE PARENTERAL SOLUTION AND METHOD FOR MAKING THE SAME

RELATED APPLICATION

The present application is a continuation-in-part of U.S. patent application Ser. No. 09/822,767, filed on Mar. 29, 2001, which is expressly incorporated herein by reference.

TECHNICAL FIELD

This invention relates generally to a premixed pharmaceutical composition containing amiodarone for parenteral administration. Particularly, the composition, and method for making the same, provides an enhanced shelf-life and an improved polymeric container compatibility over diluted formulations.

BACKGROUND ART

Amiodarone HCl (2-butyl-3-benzofuranyl) [4-[2-(diethylamino)ethoxy]-3,5-diiodophenyl]methanone hydrochloride, is a class III antiarrhythmic agent that possesses electro physiologic characteristics of all four Vaughan Williams classes. The hydrochloride salt is currently marketed in ampoules suitable for intravenous administration following dilution in dextrose (CORDARONE® IV, Wyeth-Ayerst). Each milliliter of a CORDARONE® ampoule contains 50 mg amiodarone HCl, 20.2 mg benzyl alcohol, 100 mg polysorbate 80, and water for injection. The pH of the commercial product after dilution in dextrose is approximately 3.8–4.0.

One inconvenience of the prior art product is a required step of admixing 1–6 ampoules in dextrose prior to administration. Since amiodarone can be used under emergency conditions to rapidly stabilize a patient's acute ventricular arrhythmia, this dilution step consumes valuable time. Other drawbacks of the admixing step include the possibility of dosage error, needle sticks, and/or solution contamination.

Another drawback of the prior art product is that the diluted formulations have a limited shelf life at room temperature. Generally, due to diminished sterility precautions brought about by opening the sterile container of the concentrate, the resulting diluted formulations must be used within 24 hours of dilution or be discarded. Obviously, such discarded quantities of the product increase costs for healthcare providers.

An additional drawback is that the diluted formulations have been shown to be incompatible with certain polymeric materials due to drug adsorption. This phenomenon creates dosing problems for health care providers, or requires the use of special material containers for dilution and delivery.

The product configuration and amiodarone formulations described in the present invention overcome these disadvantages. The ready-to-use premixed product configuration prevents loss of time spent diluting the concentrate, avoids potential problems of contamination, helps reduce use of sharp needles, decreases medical waste production, and eliminates dosage errors. Such benefits are due to the fact that medical personnel will be able to simply use a prepared container of the inventive composition off the shelf, as needed, without additional preparation. Moreover, the new premixed amiodarone formulations have an enhanced shelf life and an improved compatibility with polymeric container materials.

U.S. Pat. No. 6,143,778 issued Nov. 7, 2000, to Gautier et al. discloses an amiodarone composition concentrate for parenteral delivery after dilution. The disclosed composition requires a physiologically acceptable buffer solution capable of solubilizing the active principle and of maintaining the pH of the concentrated composition between 2.4 and 3.8 (Gautier et al., column 4, lines 8–54). Gautier et al. disclose an amiodarone hydrochloride formulation "which is at the same time concentrated, stable and dilutable." (See column 1, lines 28–31, column 3, lines 34–39, and lines 47–56). Gautier et al., therefore, focus on the stability and admixing of the concentrate. The invention of this application provides a premixed amiodarone hydrochloride formulation which does not require dilution and does not utilize a buffer, not even for solubilizing the active, before parenteral administration to a patient.

Discussion regarding diluted amiodarone concentrations (i.e., admixtures) are set forth by Gautier et al., but no information is provided discussing the long-term stability (1 year or more) of the diluted product (column 5, lines 32–51). In the examples of a diluted form of the amiodarone, Gautier et al. teach pH levels of around 4 (see examples 2, 4, and 6 of Table, column 6, lines 45–53). Gautier et al. fail to appreciate the importance of a limited pH range of from about 2.9 to about 3.2, and preferably a pH of about 3.1 for long term stability and container compatibility of a diluted premix formulation. By focusing on the stability of a concentrate which is capable of dilution for immediate use or discard, Gautier et al. ignore the potential long term stability problems of the diluted product. That is, outside of the very narrow pH range, problems with drug degradation, particle formation, impurity formation, and container incompatibility can result. By addressing and solving these problems, the premix formulation of the present invention differs from Gautier et al.'s disclosure of both a concentrate and a diluted admix product.

Similarly, U.S. Pat. No. 5,234,949 issued Aug. 10, 1993, to Ehrenpreis et al., teaches a parenteral solution of amiodarone in acetate buffer. Ehrenpreis et al. disclose a preferred pH in the range of 3.5 to 3.8 (column 3, lines 53–54). This approach is contrary to the claimed composition and methods of the present invention.

SUMMARY OF THE INVENTION

The present invention provides a new, ready-to-use premixed formulation of amiodarone, or pharmaceutically acceptable salts thereof, which are suitable for intravenous administration and continuous infusion. Within a specific pH range of from about 2.9 to about 3.2, these formulations have an enhanced shelf life and are more compatible with polymeric container materials.

In one aspect of the invention a parenteral solution for intravenous administration is provided having amiodarone as an active ingredient. The active is solubilized in a solution of water for injection and about 0.4–12 mg/ml of a non-ionic surfactant to a concentration range of from 0.2 to 6 mg/ml, wherein the solution requires no dilution before administering and has a pH within the range of from about 2.9 to about 3.2. Optionally, an osmotic agent may also be added to the solution.

In still other aspects, at room temperature, the solution exhibits drug degradation of less than 3% per year, drug loss due to adsorption by polymeric material containers of less than 3% given a plastic surface area to solution volume ratio of approximately 4 $cm^{-1}$, minimal insoluble particulate formation, and a rate of total impurity formation of less than 0.02% (w/v) total impurities/week.

In a method for producing an amiodarone solution suitable for intravenous administration, the present invention discloses the steps of providing, as an active ingredient, an effective amount of an amiodarone solution. The active ingredient is solubilized in a water/surfactant solution, then cooled before diluting the premix solution. Optionally, an osmotic agent may be added to the solution at this point. The pH is then adjusted with a suitable pH adjuster to be within the range of from about 2.9 to about 3.2, most preferably about 3.1. The premix is then further diluted with water for injection to the final active ingredient concentration. Proper containers are then filled with the final solution which may be administered directly to a patient without further dilution.

Other advantages and aspects of the present invention will become apparent upon reading the following detailed description of the invention in conjunction with the appended drawings and claims.

BRIEF DESCRIPTION OF THE DRAWINGS

For further facilitating the understanding of the present invention, four drawing figures are appended hereto, wherein.

DETAILED DESCRIPTION

Figure 1:
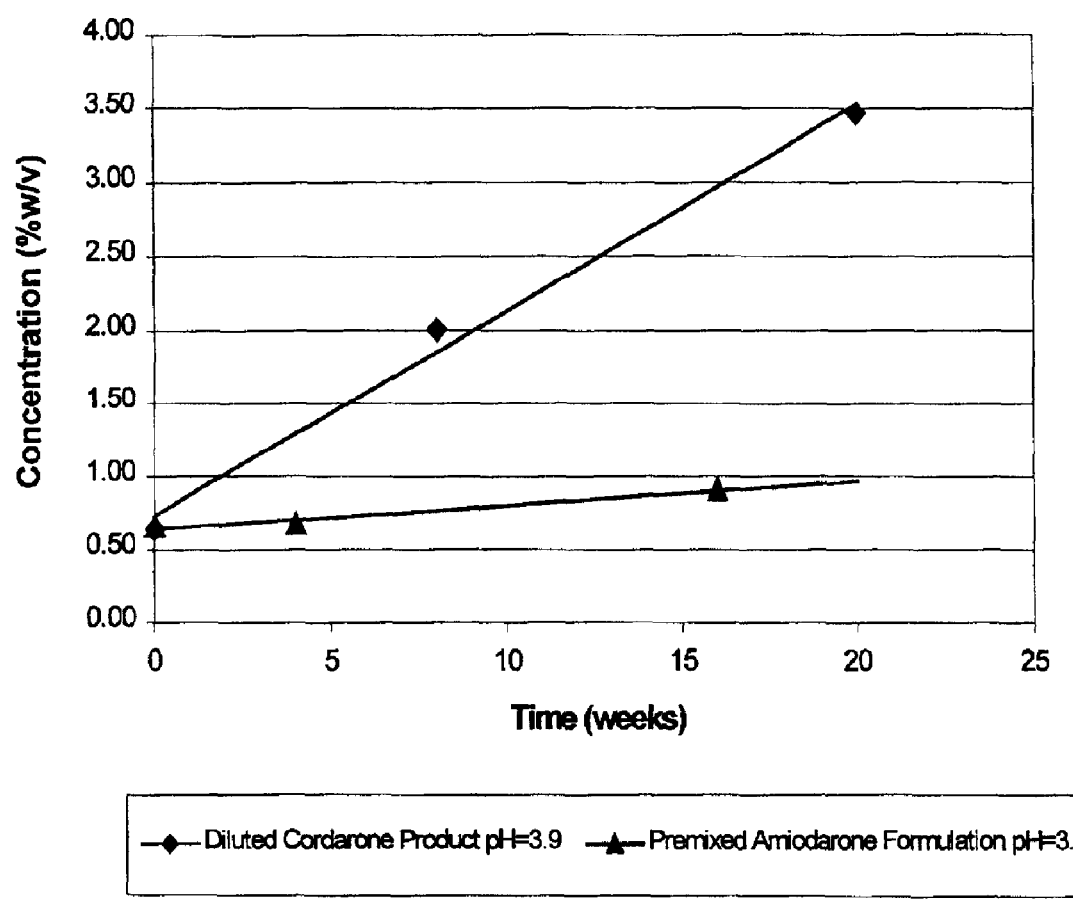
FIG. 1 is a diagrammatic illustration comparing rates of total impurity formation for diluted CORDARONE® product (pH=3.9) and premixed amiodarone formulation (pH=3.0) at 25° C. in a glass container.

While this invention is susceptible of embodiment in many different forms, this disclosure will describe in detail preferred embodiments of the invention. The present disclosure is to be considered as an example of the principles of the invention, and is not intended to limit the broad aspect of the invention to the embodiments illustrated.

According to the present invention, there is provided premixed parenteral formulations containing as an active ingredient a substituted benzofuran drug. The active ingredient has the following structural formula:

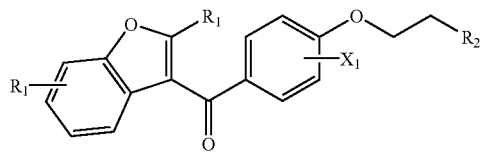

where $R_i$ represents one or more groups selected from alkyl, aryl, alkoxy, aryloxy or halogen substituents; $R_1$ represents an alkyl, aryl, alkoxy, aryloxy or halogen substituent, $X_j$ includes one or more iodo or bromo substituents on the phenyl ring; $R_2$ represents a dialkylamino group such as N,N-dimethylamino or N,N-diethylamino; $R_2$ can also be a 1-substituted heterocycle such as 1-morpholinyl, 1-piperazinyl, or 1-piperadinyl.

Amiodarone and/or one or more pharmaceutically acceptable salts thereof, are preferred for use in the present invention. Amiodarone has the following structural formula:

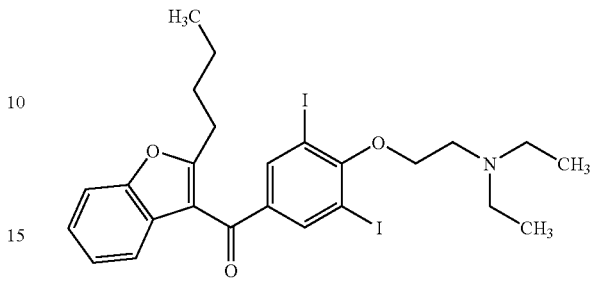

Suitable amiodarone is sold by ISOCHEM, France. The preferred concentration of amiodarone is about 0.2–6 mg/ml. The formulations also contain approximately 0.4–12 mg/ml of a non-ionic surfactant, such as an ethoxylated polysorbate (e.g., polysorbate 80), an ethylene oxide/propylene oxide copolymer, a polyethoxylated castor oil, and/or a polyethylene glycol hydroxystearate such as PEG-660 12-hydroxy stearate. The non-ionic surfactant is preferably either polysorbate 80 (TWEEN$_{80}$®) or polyethylene glycol hydroxystearate (SOLUTOL®HS-15). The solutions can also optionally include an osmotic agent such as dextrose, mannitol, sorbitol, glycerol, amino acids such as glycine, or salts such as sodium chloride. The solutions have a pH preferably within the range of from about 2.9 to about 3.2, with an initial pH of about 3.1 being the optimal pH for the solution. This initial pH range is preferred because the parenteral formulations are particularly stable, demonstrating a low percentage of drug degradation (See FIGS. 1 and 2), minimal drug adsorption to polymeric container materials (See FIG. 3), and minimal particle formation (See FIG. 4).

The present invention also provides a method for producing amiodarone solutions suitable for intravenous administration. The method comprises the steps of: (1) providing an effective ingredient or ingredients of an amiodarone solution; (2) providing water for injection[1]; (3) providing a non-ionic surfactant, such as TWEEN$_{80}$® or SOLUTOL® HS-15; (4) mixing an effective amount of the non-ionic surfactant with heated, water for injection; (5) solubilizing an effective amount of the active ingredient in the heated water/surfactant solution; (6) cooling and diluting the solution; (7) adjusting the initial pH of the solution with a suitable pH adjuster to be within the range of from approximately 2.9 to approximately 3.2; (8) diluting the solution to the final active ingredient concentration with water for injection; (9) filling suitable containers with the solution. The pH may change slightly from the initial pH, but should remain within the stated range.

[1] By "water for injection" it is meant clear, colorless, and odorless water containing no added substances and purified by distillation or reverse osmosis (See *Physician's Desk Reference*). Water for injection is typically intended for use as a solvent for the preparation of parenteral solutions. Other methods, including those developed in the future, which reasonably achieve such a standard are intended to be included under this definition.

Optionally, the method can also include the step of mixing into the solution an osmotic agent such as dextrose, mannitol, sorbitol, glycerol, amino acids, inorganic salts, and any combination of these osmotic adjusters. Further, the method can also include the step of sterilizing the solution either before or after the filling step, by any suitable sterilization method including heat, radiation, high or low energy electron-beam sterilization, or through the use of filter membrane sterilization. Presently, sterilization is achieved and maintained through an aseptic fill process similar to that described in U.S. Pat. No. 4,695,337 to Christine, and U.S. Pat. Nos. 4,761,197 and 4,964,944 both to Christine et al, each assigned to the Assignee of the present invention. The disclosure of each of these references is hereby incorporated by reference. Other terminal sterilization processes known to those skilled in the art may also be applicable.

When prepared using the disclosed methods, at room temperature, the present premix solution exhibits drug degradation of less than 3% per year, drug loss due to adsorption by polymeric material containers of less than 3% given a plastic area to solution volume ratio of approximately 4 $cm^{-1}$, minimal insoluble particulate formation, and a rate of total impurity formation of less than 0.02% (w/v) total impurities/week. These surprising results are a striking improvement over the currently available commercial product requiring dilution before administration.

The following is a non-limiting example of the present invention and should not be construed in a manner to narrow the scope of the present invention.

EXAMPLE

Preparation of Amiodarone Premixed Formulation

To a 20-L jacketed tank reactor is added 6 L of distilled, deionized water. To this is added 54 g of Tween 80 and the mixture was brought to 55° C. 27 g of amiodarone hydrochloride is added to the mixture and agitated to dissolution. The mixture is then cooled to 30° C., and 681 g of anhydrous dextrose is added and agitated to dissolution. The mixture is then preferably diluted to 13.5 L and the solution pH adjusted to 3.0 with 1 N sodium hydroxide and/or 1 N hydrochloric acid. The solution can then be diluted to 15 L with distilled, deionized water. This provides a solution having an approximate drug concentration of 1.8 mg/mL and a pH=3.0.

Figure 2:
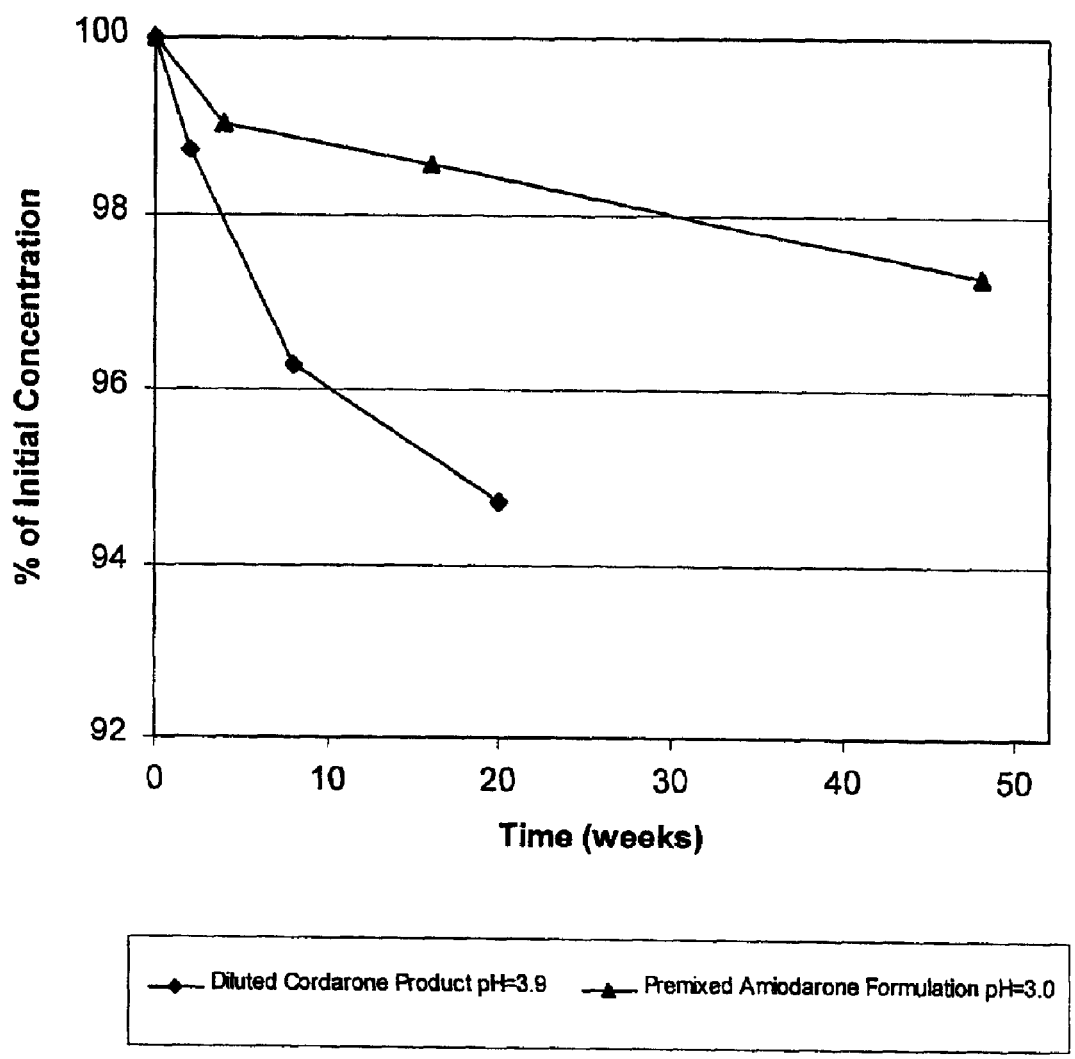
FIG. 2 is a diagrammatic illustration comparing the rates of amiodarone active degradation over a period of five months to one year for the diluted CORDARONE® product (pH=3.9) and premixed amiodarone formulation (pH=3.0) at 25° C. in a plastic container.

Amiodarone formulations prepared as described above were found to be more stable than the currently marketed CORDARONE® product following dilution. FIG. 1 shows the rate of formation of total impurities in the diluted CORDARONE® product (pH=3.9) versus the new premixed amiodarone formulation (pH=3.0) at 25° C. Both formulations were stored in a glass container. Under these conditions, the rate of total impurity formation in the CORDARONE® product and the new amiodarone premix of the present inventors is found to be approximately 0.142% and 0.016% (w/v) total impurities/week, respectively. FIG. 2 shows the rate of amiodarone active degradation over a period of five months to one year for the diluted CORDARONE® product following admixing (pH=3.9) and premixed amiodarone formulation of the present invention (pH=3.0) at 25° C. in a plastic container. Consequently, the new premixed amiodarone formulation is significantly more chemically stable than the currently marketed CORDARONE® product following admixing stored under the same conditions.

Plastic containers suitable for the present invention include those marketed by the assignee of the present application under the tradenames GALAXY™, INTRAVIA™ and VIAFLEX™.

These containers are disclosed in U.S. Pat. No. 4,686,125 to Johnston et al., U.S. Pat. No. 4,692,361 to Johnston et al., U.S. Pat. No. 4,779,997 to Schmidt, U.S. Pat. No. 5,849,843 to Laurin et al., U.S. Pat. No. 5,998,019 to Rosenbaum et al., U.S. Pat. No. 6,168,862 to Rosenbaum et al, and Des. 324,566 to Schmidt et al. Each of these patents is hereby incorporated by reference. Additionally, European application publication no. EP 0902144.9 illustrates an alternative container. It is contemplated, however, that most plastic containers will produce comparable results.

Figure 3:
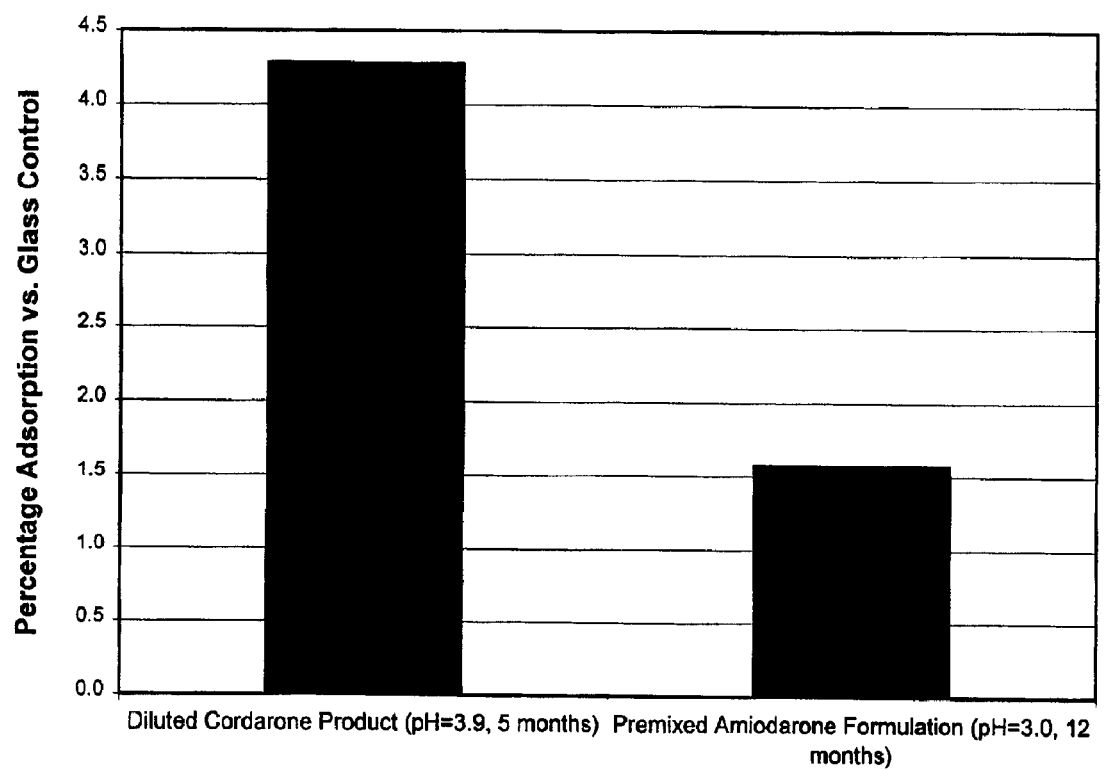
FIG. 3 is a diagrammatic illustration comparing percentages of drug adsorption at 25° C. after a period of five months to one year in a plastic container for diluted CORDARONE® product (pH=3.9) and premixed amiodarone formulation (pH=3.0)

Amiodarone formulations prepared as described were also found to be more compatible with polymeric container materials in comparison to the currently marketed diluted CORDARONE® product. FIG. 3 shows the percentage loss of amiodarone due to adsorption after a period of five months to one year storage in a plastic container at 25° C. The drug concentration, polysorbate 80 concentration, container configuration, and solution volume were virtually identical for both formulations. Under these conditions, the percentage of drug adsorption for the CORDARONE® product (pH=3.9) and the new amiodarone premix formulations (pH=3.0) is found to be approximately 4.3% and 1.6%, respectively. Consequently, significantly less drug binding to the polymeric material is observed with the new premixed amiodarone formulation.

Figure 4:
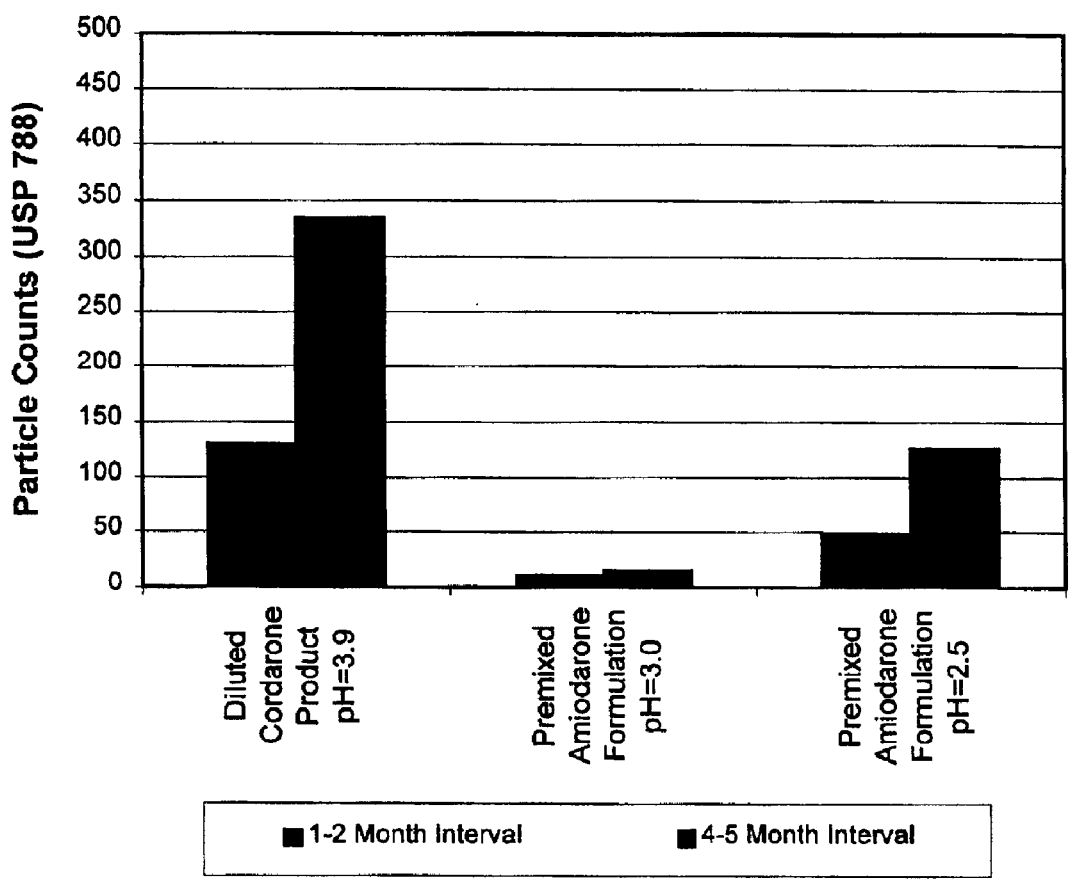
FIG. 4 is a diagrammatic illustration comparing particle counts (USP 788) after a period of one to two months and a period of four to five months for diluted CORDARONE® product (pH=3.9) and premixed amiodarone formulation (pH=3.0 and 2.5) in a plastic container.

Amiodarone formulations prepared as described above also formed less particulate matter over time in comparison to the currently marketed CORDARONE® product following admixing. FIG. 4 shows the 5 µm particle counts measured by the light obscuration particle count test (USP 788) after a period of one to two months and four to five months in a plastic container at 25° C. for the marketed CORDARONE® product following admixing (pH=3.9) and the new premixed amiodarone formulations (pH=3.0 and 2.5). The total insoluble particle count is minimal for the present invention, preferably forming less than 150 particles, more preferably less than 100 particles, and most preferably less than 50 particles over time. The least number of particles were observed in the more preferred pH range (pH=2.9–3.2) for the present invention. Similar trends were observed in the 2 µm and 10 µm particle size channels.

While the specific embodiments have been illustrated and described, numerous modifications come to mind without significantly departing from the spirit of the invention and the scope of protection is only limited by the scope of the accompanying claims.

We claim:

1. A solution for intravenous administration comprising:
    amiodarone, as an active ingredient, solubilized to a concentration range of from 0.2 to 6 mg/ml. in a solution of water for injection and a non-ionic surfactant;
    optionally, an osmotic agent; and
    wherein the solution requires no dilution before administering and has a pH within the range of from about 2.9 to about 3.2.

2. The solution of claim 1 wherein the osmotic agent is selected from the group consisting of dextrose, mannitol, sorbitol, glycerol, amino acids such as glycine, and salts such as sodium chloride.

3. The solution of claim 1 wherein the quantity of non-ionic surfactant is in the range of from about 0.4 to about 12 mg/ml.

4. The solution of claim 3 wherein the non-ionic surfactant is selected from the group consisting of an ethoxylated polysorbate such as polysorbate 80, an ethylene oxide/propylene oxide copolymer, a polyethoxylated castor oil, and a polyethylene glycol hydroxystearate such as SOLUTOL® HS-15.

5. The solution of claim 4 wherein the non-ionic surfactant is polysorbate 80.

6. The solution of claim 4 wherein the non-ionic surfactant is a polyethylene glycol hydroxystearate.

7. The solution of claim 1 wherein the pH of the solution is about 3.1.

8. The solution of claim 2 wherein the pH of the solution is about 3.1.

9. The solution of claim 3 wherein the pH of the solution is about 3.1.

10. The solution of claim 4 wherein the pH of the solution is about 3.1.

11. A solution for intravenous administration comprising:
amiodarone, as an active ingredient, solubilized to a concentration range of from 0.2 to 6 mg/ml. in a solution of water for injection and a non-ionic surfactant;
optionally, an osmotic agent; and
wherein the solution is a sterilized premix and has a pH within the range of from about 2.9 to about 3.2.

12. The solution of claim 11 wherein the pH of the sterilized premix is about 3.1.

13. The solution of claim 11 wherein the sterilized premix is refrigerated.

14. The solution of claim 13 wherein the sterilized premix is maintained at a temperature within the range of from 3 to about 10° C.

15. A solution for intravenous administration comprising:
amiodarone, as an active ingredient, solubilized in a solution of water for injection and a non-ionic surfactant and wherein the solution requires no dilution before administering, has a pH within the range of from about 2.9 to about 3.2 and has a drug degradation over time of less than 3% per year at room temperature.

16. The solution of claim 15 wherein the pH of the solution is about 3.1.

17. A solution for intravenous administration comprising:
amiodarone, as an active ingredient, solubilized to a concentration range of from 0.2 to 6 mg/ml. in a solution of water for injection and a non-ionic surfactant;
optionally, an osmotic agent; and
wherein the solution requires no dilution before administering, has a pH within the range of from about 2.9 to about 3.2 and has a rate of total impurity formation of less than about 0.02% (w/v) total impurities/week at room temperature.

18. The solution of claim 17 wherein the pH of the solution is about 3.1.

19. The solution of claim 17 wherein on the osmotic agent is selected from the group consisting of dextrose, mannitol, sorbitol, glycerol, amino acids such as glycine, and salts such as sodium chloride.

20. The solution of claim 17 wherein the quantity of non-ionic surfactant is in the range of from about 0.4 to about 12 mg/ml.

21. The solution of claim 20 wherein the non-ionic surfactant is selected from the group consisting of an ethoxylated polysorbate such as polysorbate 80, an ethylene oxide/propylene oxide copolymer, a polyethoxylated castor oil, and a polyethylene glycol hydroxystearate such as SOLUTOL® HS-15.

22. A solution for intravenous administration comprising:
amiodarone, as an active ingredient, solubilized to a concentration range of from 0.2 to 6 mg/ml. in a solution of water for injection and a non-ionic surfactant;
optionally, an osmotic agent; and
wherein the solution requires no dilution before administering, has a pH within the range of from about 2.9 to about 3.2 and has a drug adsorption of less than 3% in a plastic container which has a plastic surface area to solution volume ratio of approximately 4 $cm^{31}$ 1 at room temperature.

23. The solution of claim 22 wherein the pH of the solution is about 3.1.

24. A solution for intravenous administration consisting of:
amiodarone, as an active ingredient, solubilized to a concentration range of from 0.2 to 6 mg/ml. in a solution of water for injection and about 0.4–12 mg/ml of a non-ionic surfactant;
optionally, an osmotic agent; and
wherein the solution has a pH within the range of from about 2.9 to about 3.2.

25. The solution of claim 24 wherein the pH of the solution is about 3.1.

26. The solution of claim 25 the osmotic agent is selected from the group consisting of dextrose, mannitol, sorbitol, glycerol, amino acids such as glycine, and salts such as sodium chloride.

27. The solution of claim 25 wherein the non-ionic surfactant is selected from the group consisting of an ethoxylated polysorbate such as polysorbate 80, an ethylene oxide/propylene oxide copolymer, a polyethoxylated castor oil, and a polyethylene glycol hydroxystearate such as SOLUTOL® HS-15.

28. A solution for intravenous administration comprising:
amiodarone, as an active ingredient, solubilized to a concentration range of from 0.2 to 6 mg/ml. in a solution of water for injection and a non-ionic surfactant;
optionally, an osmotic agent; and
wherein the solution requires no dilution before administering, has a pH within the range of from about 2.9 to about 3.2 and has minimal insoluble particle formation in a plastic container at room temperature.

29. The solution of claim 28 wherein the pH of the solution is about 3.1.

* * * * *

UNITED STATES PATENT AND TRADEMARK OFFICE
CERTIFICATE OF CORRECTION

PATENT NO. : 7,067,143 B2
APPLICATION NO. : 09/945374
DATED : June 27, 2006
INVENTOR(S) : Doty et al.

It is certified that error appears in the above-identified patent and that said Letters Patent is hereby corrected as shown below:

On the cover page, item [*]

Delete the phrase "by 0 days" and insert -- by 298 days --

Signed and Sealed this

Eighth Day of April, 2008

JON W. DUDAS
*Director of the United States Patent and Trademark Office*